US010470468B2

(12) United States Patent
Suranyi et al.

(10) Patent No.: US 10,470,468 B2
(45) Date of Patent: Nov. 12, 2019

(54) MIXTURES OF SABADILLA OIL AND FUNGICIDES AND USES THEREOF

(71) Applicant: McLaughlin Gormley King Company, Golden Valley, MN (US)

(72) Inventors: Robert A. Suranyi, Minneapolis, MN (US); Darrick David Unger, Minnetonka, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 0 days.

(21) Appl. No.: 15/949,182

(22) Filed: Apr. 10, 2018

(65) Prior Publication Data

US 2018/0289019 A1    Oct. 11, 2018

Related U.S. Application Data

(60) Provisional application No. 62/483,986, filed on Apr. 11, 2017.

(51) Int. Cl.
*A01N 65/40* (2009.01)
(52) U.S. Cl.
CPC ................... *A01N 65/40* (2013.01)
(58) Field of Classification Search
CPC ........ A01N 65/40; A01N 37/36; A01N 43/40; A01N 43/54; A01N 43/653; A01N 47/16; A01N 63/00

USPC ......................................... 504/101
See application file for complete search history.

(56) References Cited

U.S. PATENT DOCUMENTS

| 3,078,211 | A | 2/1963 | Allison |
| 8,124,566 | B2 | 2/2012 | Walter et al. |
| 2009/0306189 | A1* | 12/2009 | Raemaekers .......... A01N 63/02 514/44 R |
| 2010/0297259 | A1 | 11/2010 | Wilson et al. |
| 2015/0282483 | A1* | 10/2015 | Sawada .................. A01N 43/56 504/100 |
| 2016/0081335 | A1 | 3/2016 | Van Den Eynde et al. |

FOREIGN PATENT DOCUMENTS

WO    2017/070437 A1    4/2017

OTHER PUBLICATIONS

International Search Report and Written Opinion for corresponding PCT Application No. PCT/US18/26807 dated Jul. 2, 2018.

* cited by examiner

*Primary Examiner* — Johann R Richter
*Assistant Examiner* — Courtney A Brown
(74) *Attorney, Agent, or Firm* — Wood, Phillips, Katz, Clark & Mortimer

(57) ABSTRACT

The present invention is directed to pesticidal mixtures comprising sabadilla oil and at least one fungicide and methods of controlling pests including pathogenic fungi by application of pesticidal mixtures comprising sabadilla oil and at least one fungicide.

17 Claims, No Drawings

MIXTURES OF SABADILLA OIL AND FUNGICIDES AND USES THEREOF

CROSS-REFERENCE

This application claims priority of Provisional Application Ser. No. 62/483,986, filed Apr. 11, 2017.

FIELD OF THE INVENTION

The present invention is directed to pesticidal mixtures comprising sabadilla oil and at least one fungicide and methods of controlling pests including pathogenic fungi by application of pesticidal mixtures comprising sabadilla oil and at least one fungicide.

BACKGROUND OF THE INVENTION

Pathogenic fungi cause disease in plants and animals. Fungal plant pathogens threaten the yield and quality of agricultural crops costing farmers millions of dollars annually. Further, some fungal plant pathogens produce mycotoxins that are toxic to animals including humans. Fungicides have been developed that control the growth of fungal plant pathogens including those that produce mycotoxins.

Pathogenic fungi cause disease in plants and animals. Fungal plant pathogens threaten the yield and quality of agricultural crops costing farmers millions of dollars annually. Further, some fungal plant pathogens produce mycotoxins that are toxic to animals including humans. Fungicides have been developed that control the growth of fungal plant pathogens including those that produce mycotoxins.

Protecting crops from fungal pathogens is essential for global food security. Fungicides play a critical role in maintaining a reliable and high quality food supply by protecting crops from fungal diseases. Over the last 200 years, disease control has been achieved mainly by the use of inorganic and synthetic fungicides. These fungicides have been very effective and relatively inexpensive in controlling plant diseases. The reliance on fungicides for crop protection also led to the development of wide-spread fungicide resistance in pathogen populations globally. Furthermore the wide-spread use of fungicides across most cropping systems and production acreage also created degrees of environmental disturbance and pollution.

Fungal pathogens remain one of the major risk factor to human welfare by exerting a continued and increasing threat to global food security. See, Savary et al., Crop losses due to diseases and their implications for global food production losses and food security, 2012 December, *Food Security*, 4(4), 519-537. Fungicides are a primary tool in controlling fungal pathogens globally. However, global effectiveness of fungicides is severely impacted by wide-spread resistance to fungicides across key fungal pathogens. The impact that fungicide resistance exerts on the global food supply is further compounded by the economic, environmental and regulatory complexities associated with the development and commercialization of new classes of fungicides that address existing resistance issues.

Fungicide resistance is a heritable change in the sensitivity of a pathogen population to the mode of action of fungicides, a change that could manifest itself either as a rapid failure of disease control or as a gradual loss of the efficacy of the compound over time. The most common mechanisms of fungicide resistance involves mutation(s) of the target site known as target site insensitivity. Mutation or alteration of the biochemical target site generally confirms resistance to multiple fungicides that share a common mode of action (cross-resistance). Furthermore, the mode of action of modern fungicides is generally highly target site specific, and thus, these compounds are at a high risk for pathogen resistance due to mutation events occurring at the target site. In addition to target site insensitivity, additional mechanisms of documented fungicide resistance include the development of alternative metabolic pathways, increased rate of detoxification of the active ingredient, and increased removal of the toxic substance via diverse physiological mechanisms.

Effective management of fungicide resistance therefore is essential for global crop production and food security. To be most effective, resistance management strategies aimed at combatting and/or delaying the development of fungicide resistance need to be integrated into a holistic program within the cropping system and employed on a regional basis to also address the rapid and long distance dispersal of many fungal pathogens.

A fundamental aspect of fungicide utilization under the broader framework of resistance management is the rotation of fungicides with different modes of action. The selection of the most appropriate rotational partner is a complex process underlined by regulatory, biochemical, and economic considerations. In general, fungicides with complex multi-site modes of action are considered to be good rotational partners because of the significantly lower probability for the pathogen population to carry multiple mechanisms of resistance. The reduced risk of resistance development against fungicides with complex multi-site mode of action is demonstrated by the continued efficacy of some of the oldest inorganic fungicides against plant pathogens, e.g., copper or lime sulfur-based fungicides. In addition to fungicides with multi-site mode of action, compounds acting via a physical mode of action also provide an important tool for the management of biochemically based mechanisms of fungicide resistance. These compounds act via a physical mode of action on the propagules of the disease organism, e.g., negatively impacting spore impingement, spore germination, and the dispersal of airborne propagules.

Additional strategies also include seasonal limitations on the number of applications, use of mixtures of fungicides with different modes of actions, maintaining the recommended dose range for the fungicide, the timing and method of application of the fungicide and the incorporation of non-chemical management tactics into the overall program. The primary tenet of resistance management is reduction of differential survival between resistant and susceptible genotypes by reducing the selection pressure exerted on the pathogen population by a particular fungicide.

Many fungicides have been developed to control these fungal plant diseases. Common fungicides include benzimidazoles, dicarboximides, demethylation inhibitors including imidazoles, piperazines, and triazoles, phenyl amides, anilinopyrimidines, quinone outside inhibitors including strobilurins, phenylpyrroles, aromatic hydrocarbons including chlorophenyls and triadiazoles, cinnamic acid, hydroxyanilide, phosphonate, dithiocarbamate, chloroalkythios and chloronitriles. However, these fungicides have limited efficacy. Further, many plant diseases have developed resistance to these fungicides.

In contrast, botanically-sourced active ingredients are generally readily biodegradable and significantly less harmful to the environment. Unlike conventional fungicides which are typically based on a single active ingredient, plant derived pesticides usually comprise of an array of chemical compounds which affect a wide range of physiological functions in the target organism. As a consequence, the probability of resistance development against botanically sourced products containing a mixtures of compounds is reduced.

Sabadilla oil is an effective naturally derived fungicide found in the tissues of many of the plants of the genus *Schoenocaulon*, commonly referred to as sabadilla. Sabadilla oil is the byproduct obtained during extraction of alkaloids from the Sabadilla plant. Sabadilla oil does not contain the alkaloids, veratridine and cevadine. The species with the longest history of use, and the most readily available, is *Schoenocaulon officinale*. The plant is indigenous to Central and South America.

Fungicides must be cost effective to warrant their use on crops. Thus, the ability to reduce the cost of these fungicides is paramount to their use. One method to reduce cost is mixing more than one fungicide into one composition prior to application to crops, thus reducing the cost of application. Further, the application of more than one fungicide helps reduce pesticide resistance.

Thus, there is a need in the art for pesticide mixtures that contain plant derived fungicides.

SUMMARY OF THE INVENTION

In one aspect, the present invention is directed to pesticidal mixtures of sabadilla oil and at least one fungicide.

In another aspect, the present invention is directed to methods of controlling fungal plant pathogens, comprising applying effective amounts of a mixture of sabadilla oil and at least one fungicide.

In a preferred aspect, the sabadilla oil is derived from *Schoenocaulon officinale*.

In another preferred aspect, the fungicide is at least one fungicide selected from the group consisting of azoxystrobin.

DETAILED DESCRIPTION OF THE INVENTION

Applicant unexpectedly discovered that pesticidal mixtures of sabadilla oil and fungicides provided enhanced pesticidal activity compared to either pesticide alone. Application of the mixture of sabadilla oil and model synthetic fungicide(s) significantly improved the efficacy of the synthetic fungicides applied alone (mandestrobin, etc.) against key plant pathogens.

The present invention is directed to pesticidal mixtures comprising an effective amount of sabadilla oil and at least one fungicide.

Sabadilla oil may be derived from any species of *Schoenocaulon*. The genus *Schoenocaulon* includes the following species: *S. calcicola, S. caricifolium, S. comatum, S. conzattii, S. dubium* (alt. *S. gracile*), *S. framei, S. ghiesbreghtii* (alt. *S. drummondii, S. yucatanense*), *S. ignigenum, S. intermedium, S. jaliscense, S. macrocarpum* (alt. *S. lauricola*), *S. madidorum, S. megarrhizum, S. mortonii, S. oaxacense, S. obtusum, S. officinale, S. pellucidum, S. plumosum, S. pringlei, S. rzedowskii, S. tenorioi, S. tenue, S. tenuifolium, S. texanum*, and *S. tigrense*. In a preferred embodiment, the sabadilla oil is derived from *S. officinale*. Further, sabadilla oil may be obtained from any part of the plant. In a preferred embodiment the sabadilla oil is obtained from the seeds of the plant. In another preferred embodiment, the sabadilla oil is free of seed material including cellulose, hemicellulose, lignin and pectin.

Fungicides suitable for use in the mixtures of the present invention include, but are not limited to, benzimidazoles, dicarboximides, demethylation inhibitors including imidazoles, piperazines, and triazoles, phenylamides, anilinopyrimidines, quinone outside inhibitors including strobilurins, phenylpyrroles, aromatic hydrocarbons including chlorophenyls and triadiazoles, cinnamic acid, hydroxyanilide, phosphonate, dithiocarbamate, chloroalkythios and chloronitriles. In a preferred embodiment the fungicide is at least one fungicide selected from the group consisting of *Streptomyces lydicus*, metconazole, fluopicolide, fenpyrazamine, mandestrobin and azoxystrobin.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will control the target pest. The "effective amount" will vary depending on the mixture concentration, the type of pest(s) being treated, the severity of the pest infestation, the result desired, and the life stage of the pest during treatment, among other factors. Thus, it is not always possible to specify an exact "effective amount." However, an appropriate "effective amount" in any individual case may be determined by one of ordinary skill in the art.

As used herein, w/w denotes weight by weight of the total mixture.

In a preferred embodiment, the ratio of sabadilla oil to the at least one fungicide is from about 1:20 to about 200:1, more preferably from about 1:10 to about 150:1 and even more preferably from about 1:6 to about 133:1. Additionally, the ratio of sabadilla oil to the at least one fungicide from about 300:1 to about 100,000:1.

In another preferred embodiment, the pesticidal mixtures of the present invention may contain one or more excipients selected from the group consisting of solvents, anti-caking agents, stabilizers, defoamers, slip agents, humectants, dispersants, wetting agents, thickening agents, emulsifiers, penetrants, adjuvants, synergists, polymers, propellants and/or preservatives.

The present invention is further directed to methods of controlling a pest comprising applying a pesticidal mixture comprising an effective amount of sabadilla oil and at least one fungicide to the pest or the pest's environment.

In a preferred embodiment, the pest is a pathogenic fungus, more preferably a fungal plant pathogen.

The pesticidal mixtures of the present invention can be applied by any convenient means. Those skilled in the art are familiar with the modes of application including spraying, brushing, soaking, in-furrow treatments, pressurized liquids (aerosols), fogging or side-dressing.

In a preferred embodiment, sabadilla oil is applied to the pest or the pest's environment at a rate from about 1 to about 10,000 grams per hectare ("g/HA"), preferably from about 1 to about 1,000 g/HA and more preferably from about 100 to about 1,000 g/HA, and even more preferably from about 93.5 to about 9,353 g/HA.

In a preferred embodiment, the fungicide is applied to the pest or the pest's environment at a rate from about 0.1 to about 1,000 g/HA, more preferably from about 0.1 to about 700 g/HA and most preferably from about 0.1 to about 560 g/HA.

Table 1 below shows label application rates for particular commercially available fungicides. The list of fungicides in Table 1 below is not to be construed as limiting to the fungicides that may be included in mixtures of the present invention.

TABLE 1

Label application rates of commercially available fungicides

| Fungicide | Low rate g AI/HA | High rate g AI/HA |
|---|---|---|
| Actinovate ® AG | 0.1 | 0.3 |
| Quash ® | 70.05 | 140.11 |
| Presidio ® | 105.08 | 140.11 |
| Protexio ® | 424.08 | 555.7 |
| Pinpoint ® | 259.2 | 472.86 |

"g AI/HA" denotes grams of active ingredient per hectare

Actinovate® AG contains 0.0371% *S. lydicus* WYEC 108 and is a registered trademark of Monsanto Technology LLC and is available from Valent U.S.A. Corporation.

Quash® contains 50% metconazole and is a registered trademark and available from Valent U.S.A. Corporation.

Presidio® contains 39.5% fluopicolide and is a registered trademark and available from Valent U.S.A. Corporation.

Protexio® contains 36.13% fenpyrazamine and is a registered trademark and available from Valent U.S.A. Corporation.

Pinpoint® contains 43.4% mandestrobin and is a registered trademark and available from Valent U.S.A. Corporation.

In another preferred embodiment, pesticidal mixtures of the present invention comprise from about 0.05% to about 5.0% w/w sabadilla oil.

In another preferred embodiment, pesticidal mixtures of the present invention comprise from about 0.01% to about 1% w/w of at least one fungicide, more preferably from about 0.05% to about 0.5% w/w.

As used herein, "control" a pest or "controlling" pest(s) refers to killing, incapacitating, repelling, or otherwise decreasing the negative impact of the pest on plants or animals to a level that is desirable to the grower or animal.

As used herein, "pest's environment" refers to any area that the pest is present during any life stage. One environment likely to be treated by the methods of the present invention includes the plants and plant propagation materials that the pest is living on and the surrounding soil. The pest's environment may also include harvested plants, gardens, fields, greenhouses, or other buildings, and various indoor surfaces and structures, such as furniture including beds, and furnishings including books, clothing, etc.

The articles "a," "an" and "the" are intended to include the plural as well as the singular, unless the context clearly indicates otherwise. For example, the methods of the present invention are directed to controlling "pest" but this can include control of a multiple pests (such as a more than one pathogenic fungus or more than one pathogenic fungus species).

The present invention is illustrated by the following representative examples.

EXAMPLE 1

The objective of Example 1 was to evaluate the efficacy of sabadilla oil against naturally occurring Fuchsia rust caused by the fungal pathogen, *Pucciniastrum epilobii* on Fuchsia.

Method:

Only plants showing low levels of rust infestation at the start of the trial were included in the trial. Plants were maintained in plastic pots (11 cm diameter), containing Clover™ multi-purpose, peat based compost during the study. Plants were maintained under optimal growing conditions. No other plant protection products were applied during the study.

Sabadilla oil was applied as an emulsion concentrate (EC) formulation containing 70% sabadilla oil at 2.0 and 4.0% v/v concentrations. During the course of the study, a total of five treatment applications were made at 7 days' intervals. All treatment applications were made using a pressurized CP1.5 Cooper Pegler Compression Hand sprayer. The spray equipment was fully calibrated to obtain complete coverage of the plants. Each treatment was replicated five times. Each replicate consisted of one plant (Fuchsia 'Tom West' Meillez (v)), which were at growth stage BBCH 32-34 (two to four visibly extended internodes). The treatments were arranged in a randomized block design within the greenhouse.

An initial assessment of rust infestation was recorded at 0-day. Plots were arranged to ensure an even distribution of infection prior to treatment application. Efficacy data was collected 1DAA (day after application), 3DAA, 7DAA, 14DAA, 21DAA, 28DAA, and 35DAA. The following variables were assessed: 1) percentage leaf area affected on 5 randomly selected leaves per plant; 2) percentage of leaves infected per plant (14DAA onwards); 3) phytotoxicity; and 4) plant vigor.

Data were analyzed using analysis of variance (ANOVA). Tukey Kramer HSD comparison tests were used to distinguish between treatment means.

For each treatment, the corrected percentage control of rust was calculated relative to untreated control plots by means of the Henderson-Tilton formula (Henderson, C. F. and E. W. Tilton, 1955. J. Econ. Entomol. 48:157-161):

$$\text{Corrected \% control}=1-(Ta/Ca)\times(Cb/Tb)\times 100$$

Where:

Ta=Mean % leaf area affected in treated plots after application

Ca=Mean % leaf area affected in control plots after application

Cb=Mean % leaf area affected in control plots before application

Tb=Mean % leaf area affected in treated plots before application

Results:

Sabadilla oil treatments did not show negative impact on plant vigor. Similarly, no phytotoxicity was observed on plants exposed to sabadilla treatments.

The percentage of leaf area affected by rust was similar in all treatments prior to treatment application.

Sabadilla oil applied at 2.0% showed significant reduction of the development of rust infection in Fuchsia plants by 14-days relative to the control. Sabadilla oil applied at 4.0% also showed numerically superior performance to the control but the difference was not significant. However, by 28-days both sabadilla oil treatments provided a significant control of rust infestations (Table 1).

TABLE 1

Efficacy of sabadilla oil in controlling *Fuchsia* rust (mean percentage of affected leaf area).

| | Treatment | | | | | | | |
|---|---|---|---|---|---|---|---|---|
| | 0DAA[1] | 1DAA | 3DAA | 7DAA | 14DAA | 21DAA | 28DAA | 35DAA |
| | | | | | Date | | | |
| | 6 Nov. 2015 | 7 Nov. 2015 | 9 Nov. 2015 | 13 Nov. 2015 | 20 Nov. 2015 | 27 Nov. 2015 | 4 Dec. 2015 | 11 Dec. 2015 |
| Water Control | 1.12 A | 0.88 A | 1.44 A | 2.96 A | 6.12 A | 7.24 A | 6.08 A | 6.16 A |
| Sabadilla oil at 2% v/v | 1.04 A | 1.20 A | 1.20 A | 1.72 A | 1.76 B | 1.84 B | 0.88 B | 0.92 B |
| Sabadilla oil at 4% v/v | 1.00 A | 1.20 A | 1.00 A | 2.04 A | 2.00 AB | 2.12 AB | 1.40 B | 1.16 B |

[1]Values followed by the same letter are not significantly different (Tukey-Kramer HSD comparison tests, $P \geq 0.05$).

In terms of the frequency of rust infestation per plant, sabadilla oil provided approximately 3-5× reduction of rust infestation but these differences were not significant ($P \geq 0.05$) (Table 2). However, the data clearly demonstrates that applications of sabadilla oil reduce the spread of the disease within the canopy.

TABLE 2

Efficacy of sabadilla oil in controlling *Fuchsia* rust (mean percentage of leaf infected per plant).

| | Treatment | | | |
|---|---|---|---|---|
| | 14DAA | 21DAA | 28DAA | 35DAA |
| | | Date | | |
| | 20 Nov. 2015 | 27 Nov. 2015 | 4 Dec. 2015 | 11 Dec. 2015 |
| Water Control | 29.0 A | 35.0 A | 32.0 A | 33.0 A |
| Sabadilla oil at 2% v/v | 12.0 A | 9.4 A | 5.8 A | 5.8 AB |
| Sabadilla oil at 4% v/v | 14.4 A | 13.4 A | 11.4 A | 9.4 AB |

[1]Values followed by the same letter are not significantly different (Tukey-Kramer HSD comparison tests, $P \geq 0.05$).

In terms of overall control, the application of sabadilla oil provided ~80% control of rust infection by the end of the study. Furthermore, evidence of suppression of disease was already evident by 7-days and the efficacy of sabadilla oil was maintained for the remainder of the study (Table 3).

TABLE 3

Overall efficacy of sabadilla oil in controlling *Fuchsia* rust (% control).

| | Treatment | | | | | | |
|---|---|---|---|---|---|---|---|
| | 1DAA[1] | 3DAA | 7DAA | 14DAA | 21DAA | 28DAA | 35DAA |
| Water control | 0.0 | 0.0 | 0.0 | 0.0 | 0.0 | 0.0 | 0.0 |
| Sabadilla oil at 2% v/v | −46.85 | 10.26 | 37.42 | 69.03 | 72.63 | 84.41 | 83.92 |
| Sabadilla oil at 4% v/v | −52.73 | 22.22 | 22.81 | 63.40 | 67.20 | 74.21 | 78.91 |

[1]Negative values indicate zero control.

Conclusion:

Sabadilla oil applied at 2 and 4% v/v demonstrated fungicidal efficacy against rust pathogens.

EXAMPLE 2

The objective of Example 2 was to evaluate the efficacy of sabadilla oil against naturally occurring powdery mildew infection caused by fungi in the Order Erysiphales on Dahlia.

Method:

Only plants that showed low levels of powdery mildew infestation at the beginning of the study were included. Plants were maintained in plastic pots (14 cm diameter), containing Clover™ multi-purpose, peat based compost during the study. Plants were maintained under protected conditions with good light, appropriate temperature settings and sufficient watering. No other plant protection products were applied during the study.

Sabadilla oil was applied as an EC formulation containing 70% sabadilla oil at 2.0 and 4.0% v/v concentrations. During the course of the study, a total of five treatment applications were made at 7 days' intervals. All treatment applications were made using a pressurized CP1.5 Cooper Pegler Compression Hand sprayer. The spray equipment was fully calibrated to obtain complete coverage of the plants. Each treatment was replicated five times. Each replicate consisted of one plant (Dahlia, cultivar Bishop of Canterbury), which were at growth stage BBCH 22-32 (two side shoots with two visibly extended internodes). The treatments were arranged in a randomized block design within the greenhouse.

An initial assessment of powdery mildew infestation was recorded at 0-day. Plots were arranged to ensure an even distribution of infection prior to treatment application. Efficacy data was collected 1DAA (day after application), 3DAA, 7DAA, 14DAA, 21DAA, 28DAA, and 35DAA. The following variables were assessed: 1) percentage leaf area affected on 5 randomly selected leaves per plant; 2) percentage of leaves infected with powdery mildew per plant; 3) phytotoxicity; and 4) plant vigor.

Data were analyzed using analysis of variance (ANOVA). Tukey Kramer HSD comparison tests were used to distinguish between treatment means.

For each treatment, the corrected percentage control of powdery mildew was calculated relative to untreated control plots by means of the Henderson-Tilton formula (Henderson, C. F. and E. W. Tilton, 1955. J. Econ. Entomol. 48:157-161):

$$\text{Corrected \% control} = 1 - (Ta/Ca) \times (Cb/Tb) \times 100$$

Where:
Ta=Mean % leaf area affected in treated plots after application
Ca=Mean % leaf area affected in control plots after application
Cb=Mean % leaf area affected in control plots before application
Tb=Mean % leaf area affected in treated plots before application Results:

Sabadilla oil treatments did not show negative impact on plant vigor. Similarly, no phytotoxicity was observed on plants exposed to sabadilla treatments.

The percentage of leaf area affected by powdery mildew was similar in all treatments prior to treatment application.

Sabadilla oil applied at 2.0 and 4.0% showed a significant reduction of the development of powdery mildew immediately after the first treatment application. Significant control of powdery mildew was maintained throughout the course of the study by sabadilla oil treatments (Table 4).

TABLE 4

Efficacy of sabadilla oil in controlling powdery mildew (mean percentage of affected leaf area).

| | Treatment | | | | | | | |
|---|---|---|---|---|---|---|---|---|
| | 0DAA[1] | 1DAA | 3DAA | 7DAA | 14DAA | 21DAA | 28DAA | 35DAA |
| | | | | | Date | | | |
| | 6 Jul. 2016 | 7 Jul. 2016 | 9 Jul. 2016 | 13 Jul. 2016 | 20 Jul. 2016 | 27 Jul. 2016 | 3 Aug. 2016 | 10 Aug. 2016 |
| Water Control | 12.60 A | 16.20 A | 20.80 A | 27.20 A | 34.80 A | 33.60 A | 37.20 A | 34.80 A |
| Sabadilla oil at 2% v/v | 12.40 A | 3.00 B | 4.60 B | 7.60 B | 3.80 B | 1.16 B | 1.00 B | 0.88 B |
| Sabadilla oil at 4% v/v | 12.40 A | 1.60 B | 1.80 B | 1.68 BC | 0.20 C | 0.00 C | 0.00 C | 0.00 C |

[1]Values followed by the same letter are not significantly different (Tukey-Kramer HSD comparison tests, $P \geq 0.05$).

Sabadilla oil application also significantly reduced the frequency of powdery mildew infestation per plant (Table 5). This reduction of powdery mildew infection was evident immediately after the first application of sabadilla oil. Furthermore, the high efficacy of sabadilla oil against powdery mildew was maintained throughout the course of the study.

TABLE 5

Efficacy of sabadilla oil in controlling powdery mildew (mean percentage of leaf infected per plant).

| | Treatment | | | | | | |
|---|---|---|---|---|---|---|---|
| | 0DAA[1] | 1DAA | 3DAA | 7DAA | 14DAA | 21DAA | 28DAA | 35DAA |
| | | | | | Date | | | |
| | 6 Jul. 2016 | 7 Jul. 2016 | 9 Jul. 2016 | 13 Jul. 2016 | 20 Jul. 2016 | 27 Jul. 2016 | 3 Aug. 2016 | 10 Aug. 2016 |
| Water Control | 41.0 A | 50.0 A | 54.0 A | 56.0 A | 53.0 A | 50.0 A | 56.0 A | 58.0 A |
| Sabadilla oil at 2% v/v | 36.0 A | 24.0 B | 19.0 B | 25.0 B | 19.0 AB | 6.0 B | 4.0 B | 2.2 B |
| Sabadilla oil at 4% v/v | 41.0 A | 9.0 B | 6.0 B | 5.0 B | 1.0 C | 0.0 C | 0.0 B | 0.0 C |

[1]Values followed by the same letter are not significantly different (Tukey-Kramer HSD comparison tests, $P \geq 0.05$).

In terms of overall control, the application of sabadilla oil provided a very high level of efficacy against powdery mildew infection. A clear dose response was evident for the efficacy sabadilla oil treatments especially at the early stages of the study. Sabadilla oil applied at 4% v/v achieved >90% control of powdery mildew shortly after the first treatment application (3 DAA) and >90% efficacy was maintained throughout the study. Sabadilla oil applied at 2% v/v achieved >90% efficacy against powdery mildew by day 21 (Table 6).

TABLE 6

Overall efficacy of sabadilla oil in controlling powdery mildew (% control).

| | Treatment | | | | | | |
|---|---|---|---|---|---|---|---|
| | 1DAA | 3DAA | 7DAA | 14DAA | 21DAA | 28DAA | 35DAA |
| Water Control | 0.0 | 0.0 | 0.0 | 0.0 | 0.0 | 0.0 | 0.0 |
| Sabadilla oil at 2% v/v | 81.18 | 77.53 | 71.61 | 88.90 | 96.49 | 97.27 | 97.43 |
| Sabadilla oil at 4% v/v | 89.96 | 91.21 | 93.72 | 99.42 | 100.00 | 100.00 | 100.00 |

Conclusion:

Sabadilla oil applied at 2 and 4% v/v demonstrated fungicidal efficacy against powdery mildew pathogen.

What is claimed is:

1. A pesticidal mixture consisting of an effective amount of sabadilla oil, at least one fungicide selected from the group consisting of *Streptomyces lydicus*, metconazole, fluopicolide, fenpyrazamine, mandestrobin and axozystrobin and one or more excipients selected from the group consisting of solvents, anti-caking agents, stabilizers, defoamers, slip agents, humectants, dispersants, wetting agents, thickening agents, emulsifiers, penetrants, adjuvants, polymers, propellants and preservatives.

2. The mixture of claim 1, wherein the sabadilla oil is derived from *Schoenocaulon officinale*.

3. The mixture of claim 1, wherein the sabadilla oil is extracted from seeds.

4. The mixture of claim 1, wherein the sabadilla oil is at a concentration from about 0.05% to about 5.0% w/w, wherein w/w denotes weight by total weight of the mixture.

5. The mixture of claim 1, wherein the at least one fungicide is at a concentration from about 0.01% to about 1% w/w, wherein w/w denotes weight by total weight of the mixture.

6. The mixture of claim 1, wherein the ratio of sabadilla oil to fungicide is from about 1:20 to about 200:1.

7. The mixture of claim 1, wherein the ratio of sabadilla oil to fungicide is from about 1:10 to about 150:1.

8. The mixture of claim 1, wherein the ratio of sabadilla oil to fungicide is from about 1:6 to about 133:1.

9. The mixture of claim 1, wherein the ratio of sabadilla oil to fungicide is from about 300:1 to about 100,000:1.

10. A method of controlling a pest consisting of applying a pesticidal mixture consisting of an effective amount of sabadilla oil, at least one fungicide selected from the group consisting of *Streptomyces lydicus*, metconazole, fluopicolide, fenpyrazine, mandestrobin and azoxystrobin and one or more excipients selected from the group consisting of solvents, anti-caking agents, stabilizers, defoamers, slip agents, humectants, dispersants, wetting agents, thickening agents, emulsifiers, penetrants, adjuvants, polymers, propellants and preservatives to the pest or the pest's environment.

11. The method of claim 10, wherein the pest is a pathogenic fungus.

12. The method of claim 10, wherein the sabadilla oil is applied to the pest or the pest's environment at a rate from about 1 to about 10,000 grams per hectare.

13. The method of claim 10, wherein the sabadilla oil is applied to the pest or the pest's environment at a rate from about 1 to about 1,000 grams per hectare.

14. The method of claim 10, wherein the sabadilla oil is applied to the pest or the pest's environment at a rate from about 100 to about 1,000 grams per hectare.

15. The method of claim 10, wherein the fungicide is applied to the pest or the pest's environment at a rate from about 0.1 to about 1,000 grams per hectare.

16. The method of claim 10, wherein the fungicide is applied to the pest or the pest's environment at a rate from about 0.1 to about 700 grams per hectare.

17. The method of claim 10, wherein the fungicide is applied to the pest or the pest's environment at a rate from about 0.1 to about 560 grams per hectare.

\* \* \* \* \*